(12) United States Patent
Todd et al.

(10) Patent No.: US 10,548,513 B2
(45) Date of Patent: Feb. 4, 2020

(54) ACTIVITY RECOGNITION

(71) Applicant: Whoop, Inc., Boston, MA (US)

(72) Inventors: Brian Anthony Todd, Boston, MA (US); John Vincenzo Capodilupo, Boston, MA (US); Emily Rachel Capodilupo, Boston, MA (US); William Ahmed, Boston, MA (US)

(73) Assignee: Whoop, Inc., Boston, MA (US)

( * ) Notice: Subject to any disclaimer, the term of this patent is extended or adjusted under 35 U.S.C. 154(b) by 0 days.

(21) Appl. No.: 15/960,461

(22) Filed: Apr. 23, 2018

(65) Prior Publication Data

US 2018/0303381 A1 Oct. 25, 2018

Related U.S. Application Data

(60) Provisional application No. 62/510,708, filed on May 24, 2017, provisional application No. 62/489,259, filed on Apr. 24, 2017.

(51) Int. Cl.
*A61B 5/11* (2006.01)
*A61B 5/0205* (2006.01)
(Continued)

(52) U.S. Cl.
CPC .......... *A61B 5/1118* (2013.01); *A61B 5/0205* (2013.01); *A61B 5/1123* (2013.01);
(Continued)

(58) Field of Classification Search
CPC .................................................. A61B 5/1118
See application file for complete search history.

(56) References Cited

U.S. PATENT DOCUMENTS 8,855,749 B2 * 10/2014 McKenna .......... G06K 9/00557
600/473
2006/0195020 A1 * 8/2006 Martin ................... G06F 19/00
600/301
(Continued)

FOREIGN PATENT DOCUMENTS

WO    WO-2018200421    11/2018

OTHER PUBLICATIONS

Hammerla, Nils Y. et al., "Deep, Convolutional, and Recurrent Models for Human Activity Recognition using Wearables", Apr. 29, 2016 , 7 pages.
(Continued)

*Primary Examiner* — Hyun D Park
(74) *Attorney, Agent, or Firm* — Strategic Patents, P.C.

(57) ABSTRACT

A variety of techniques are used automate the collection and classification of workout data gathered by a wearable physiological monitor. The classification process is staged in order to correctly and efficiently characterize a workout type. Initially, a generalized workout event is detected using motion and heart rate data. Then a location of the monitor on a user is determined. An artificial intelligence engine can then be conditionally applied (if a workout is occurring and a suitable device location is detected) to identify the type of workout. In addition to improved speed and accuracy, a workout detection process implemented in this manner can be realized with a sufficiently small computational footprint for deployment on a wearable physiological monitor.

15 Claims, 5 Drawing Sheets

(51) Int. Cl.
    *A61B 5/00*           (2006.01)
    *G06N 3/08*           (2006.01)
    *A63B 24/00*          (2006.01)
    *G06N 3/04*           (2006.01)
    *A61B 5/024*          (2006.01)

(52) U.S. Cl.
    CPC ............ *A61B 5/681* (2013.01); *A61B 5/7267* (2013.01); *A63B 24/0062* (2013.01); *G06N 3/0454* (2013.01); *G06N 3/08* (2013.01); *A61B 5/02438* (2013.01); *A61B 2562/0219* (2013.01); *A63B 2024/0071* (2013.01); *A63B 2220/40* (2013.01); *A63B 2230/06* (2013.01)

(56) References Cited

U.S. PATENT DOCUMENTS

| | | | |
|---|---|---|---|
| 2007/0282176 A1* | 12/2007 | Shimada | G16H 40/63 600/300 |
| 2008/0183090 A1 | 7/2008 | Farringdon et al. | |
| 2009/0099462 A1 | 4/2009 | Almen et al. | |
| 2011/0003665 A1* | 1/2011 | Burton | G04F 10/00 482/9 |
| 2015/0119728 A1* | 4/2015 | Blackadar | A61B 5/7264 600/484 |
| 2016/0249174 A1 | 8/2016 | Patel et al. | |
| 2016/0374567 A1 | 12/2016 | Capodilupo et al. | |
| 2017/0039480 A1 | 2/2017 | Bitran et al. | |

OTHER PUBLICATIONS

ISA, "PCT Application No. PCT/US18/28960 International Search Report and Written Opinion dated Aug. 8, 2018", 8 pages.

\* cited by examiner

ACTIVITY RECOGNITION

CROSS-REFERENCE TO RELATED APPLICATIONS

This application claims priority to U.S. Prov. App. No. 62/489,259 filed on Apr. 24, 2017 and U.S. Prov. App. No. 62/510,708 filed on May 24, 2017. The entire content of the foregoing applications is hereby incorporated by reference.

TECHNICAL FIELD

The present disclosure generally relates to activity recognition, and more specifically to automated activity recognition for a wearable physiological monitoring device.

BACKGROUND

Physiological monitoring of an individual during different periods such as training, recovery, inactivity, and sleep is useful for assessing the individual's health and fitness. This data can also inform decision making regarding future training activities. However, an assessment may depend on correctly distinguishing between workouts and other activity, as well as distinguishing what type of workout activity the individual is undertaking. There remains a need for physiological monitoring devices that can automate the collection and classification of workout data.

SUMMARY

A variety of techniques are used automate the collection and classification of workout data gathered by a wearable physiological monitor. The classification process is staged in order to correctly and efficiently characterize a workout type. Initially, a generalized workout event is detected using motion and heart rate data. Then a location of the monitor on a user is determined. An artificial intelligence engine can then be conditionally applied (if a workout is occurring and a suitable device location is detected) to identify the type of workout. In addition to improved speed and accuracy, a workout detection process implemented in this manner can be realized with a sufficiently small computational footprint for deployment on a wearable physiological monitor.

In one aspect, a computer program product disclosed herein may include computer executable code embodied in a non-transitory computer-readable medium that, when executing on a wearable physiological monitor, performs the steps of receiving data from a number of sensors on the wearable physiological monitor, the data including accelerometer data and heart rate data acquired by the wearable physiological monitor; applying a threshold based on the accelerometer data and the heart rate data to identify two endpoints of an interval of increased physical activity indicative of a workout by a user of the wearable physiological monitor; dividing the data including the accelerometer data and the heart rate data into a number of sequential segments; applying a machine learning algorithm to the number of sequential segments of the accelerometer data to determine a probability that each one of the number of sequential segments includes data from one or more locations on a body of the user; selecting one of the one or more locations having a highest overall probability of being a current position from all of the number of sequential segments as a position of the wearable physiological monitor on the body of the user; and conditionally employing an automatic workout classification algorithm to detect a type of the workout only when the position is a wrist of the user, where the automatic workout classification algorithm includes a deep convolutional neural network trained to calculate a probability that a chunk of data including at least one of accelerometer data and heart rate data from the wearable physiological monitor during the workout is each of a number of candidate types for the workout. The automatic workout classification algorithm may detect the type of the workout based on a history of exercise for the user.

In another aspect, a method for exercise monitoring disclosed herein may include receiving data from a wearable physiological monitor, the data including accelerometer data and heart rate data acquired by the wearable physiological monitor; identifying a workout by a user of the wearable physiological monitor based on the heart rate data and the accelerometer data; determining a position of the wearable physiological monitor on a body of the user during the workout; and conditionally employing an automatic workout classification algorithm to detect a type of the workout when the position is one of a number of predetermined positions on the body for which the automatic workout classification algorithm is configured to detect the type.

Identifying the workout may include applying a threshold based on at least one of the accelerometer data and the heart rate data to select two endpoints of the workout. Determining the position of the wearable physiological monitor may include training a machine learning algorithm to estimate a probability of a location of the wearable physiological monitor on a body of the user using data from an accelerometer, applying the machine learning algorithm to a number of sequential segments of the accelerometer data from the workout, and determining the position based on one of a number of candidate positions having a highest overall probability of being an actual position of the wearable physiological monitor for the number of sequential segments. Determining the position may include identifying the position from a plurality of predetermined positions including the number of predetermined positions on the body for which the automatic workout classification algorithm is configured to detect the type. The number of predetermined positions may include one or more of a wrist and an ankle. Conditionally employing the automatic workout classification algorithm may include applying the automatic workout classification algorithm only when the position is a wrist of the user. The automatic workout classification algorithm may include a deep convolutional neural network trained to calculate a probability that a chunk of data including at least one of accelerometer data and heart rate data from the wearable physiological monitor during the workout is each of a number of candidate types for the workout. The method may further include applying the deep convolutional neural network to a number of chunks of data from the wearable physiological monitor to obtain a posterior distribution of the number of candidate types for the workout. The method may further include determining the type of the workout by selecting one of the number of candidate types in the posterior distribution having a highest probability of characterizing a workout type for the workout. The method may further include updating the automatic workout classification algorithm on a central server based on new data from a plurality of users. Determining the position of the wearable physiological monitor may include training a machine learning algorithm to identify the position and updating the machine learning algorithm on a central server based on new data from a plurality of users. The method may further include adapting the automatic workout classification algorithm to a specific user based on prior workout data for the specific user. The method may further include, when the position cannot be determined during the workout, receiving additional data from the wearable physiological monitor and identifying a second workout. The method may further include determining whether a different position for the wearable physiological monitor can provide more accurate data for the type of the workout and, when the different position can provide more accurate data, providing a notification to the user suggesting a movement of the wearable physiological monitor to the different position.

In one aspect, a system disclosed herein may include a wearable housing, one or more sensors in the wearable housing configured to provide heart rate data and accelerometer data for a user of the wearable housing, a memory, and a processor configured by computer executable code stored in the memory to identify a workout by the user based on the heart rate data and the accelerometer data, determine a position of the wearable housing on a body of the user during the workout, and conditionally employ an automatic workout classification algorithm to detect a type of the workout when the position is one of a number of predetermined positions on the body for which the automatic workout classification algorithm is configured to detect the type.

The processor may be configured to conditionally employ the automatic workout classification algorithm to detect the type of the workout only when the position is a wrist of the user. The processor may be configured to create a notification to the user to move the wearable housing to a different position when the position is not one of the number of predetermined positions on the body for which the automatic workout classification algorithm is configured to detect the type. The automatic workout classification algorithm may include a deep convolutional neural network trained to calculate a probability that a chunk of data including at least one of accelerometer data and heart rate data from the one or more sensors during the workout is each of a number of candidate types for the workout.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures. The figures are not necessarily to scale, emphasis instead being placed upon illustrating the principles of the devices, systems, and methods described herein.

DETAILED DESCRIPTION

Figure 1:
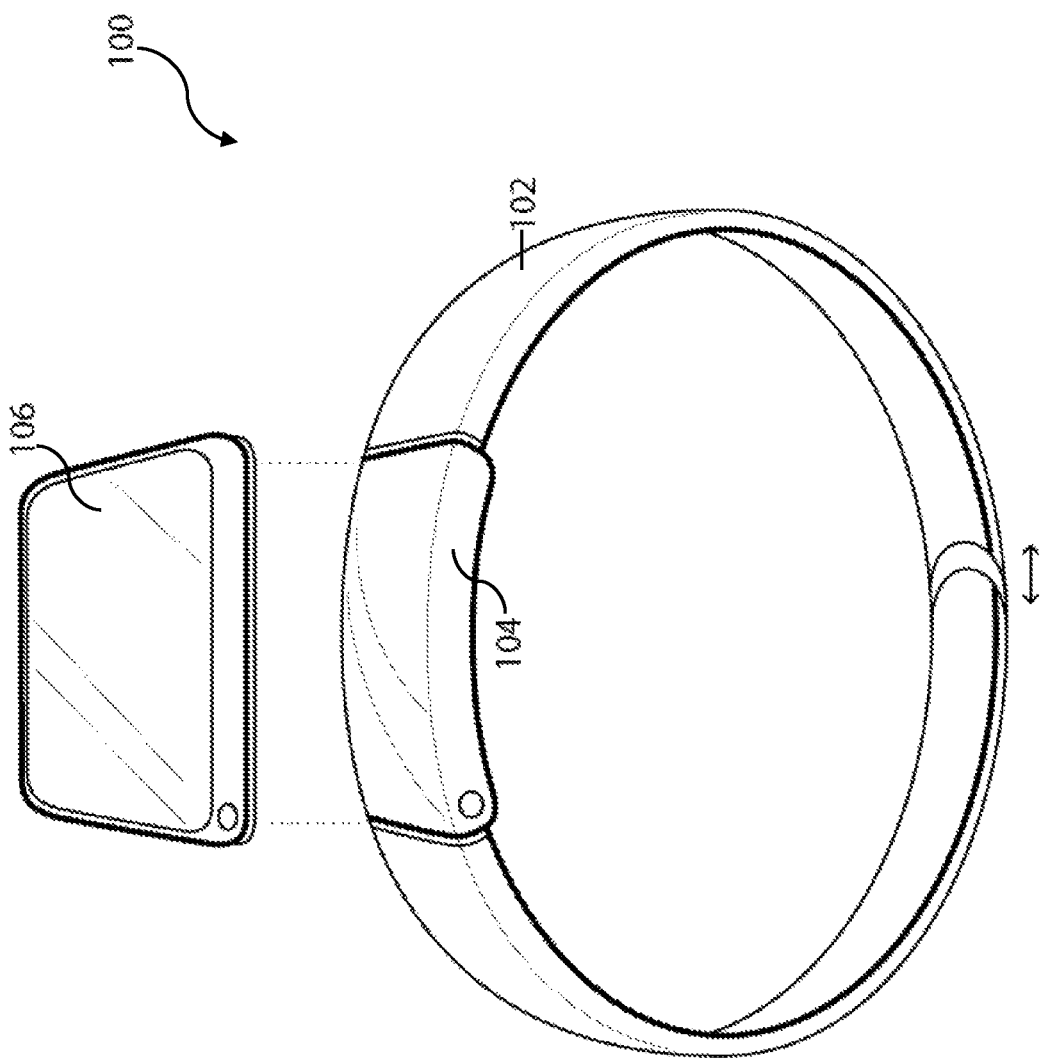
FIG. 1 illustrates a device for physiological monitoring.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value, are to be construed as indicating any deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. The use of any and all examples or exemplary language ("e.g.," "such as," or the like) is intended merely to better illuminate the embodiments and does not pose a limitation on the scope of the disclosed embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless expressly stated otherwise.

Exemplary embodiments provide physiological measurement systems, devices, and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on a user, for example, on a wrist, ankle, bicep, and the like. The term "continuous," as used herein in connection with heart rate data collection, refers to collection of heart rate data continuously over extended periods, e.g., for a day, for a night, for twenty four hours, or for more than twenty four hours, as well as to collection with sufficient resolution to enable detection of every heart beat and heart rate variability over any suitable window.

An exemplary system includes one or more light emitters for emitting light at one or more desired frequencies toward the user's skin, and one or more light detectors for received light reflected from the user's skin. The light detectors may include a photo-resistor, a photo-transistor, a photo-diode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors such as accelerometers, gyroscopes, and the like to minimize or eliminate noise in the heart rate signal caused by motion or other artifacts (or with other optical data of another wavelength), and to evaluate motion of a user, e.g., for sleep detection, device location detection, workout type detection, and so forth.

FIG. 1 illustrates a device for physiological monitoring. The device 100 may, for example, be configured as a bracelet including one or more straps 102 for securing the device 104 to a user for continuous wear. The bracelet may or may not include a display screen, e.g., a screen 106 such as a light emitting diode (LED) display for displaying any desired data (e.g., instantaneous heart rate).

The device 100 may include components configured to provide various functions such as data collection and streaming functions of the bracelet. In some embodiments, the device 100 may automatically detect when it is being worn and initiate data acquisition correspondingly. In another embodiment, the device 100 may be started and stopped manually, e.g., at the discretion of a user to begin storing information or otherwise to mark the start or end of an activity period such as sleep or a workout. In some embodiments, the button may be held to initiate a time stamp and held again to end a time stamp, which may be transmitted, directly or through a mobile communication device application, to a website as a time stamp. In another aspect, the device may not include a button, and may be controlled, e.g., remotely or through other user control techniques such as physically tapping a surface of the device.

The device 100 may include a heart rate monitor. In one example, the heart rate may be detected from the radial artery, e.g., using photoplethysmography or any other suitable technique or combination of techniques. Thus, the wearable system may include a pulse sensor such that, when a user wears the device 100 around their wrist and tightens it, the sensor portion of the device 100 is secured over the user's radial artery or other blood vessel. Secure connection and placement of the pulse sensor over the radial artery or other blood vessel may allow measurement of heart rate and pulse. It will be understood that this configuration is provided by way of example only, and that other sensors, sensor positions, and monitoring techniques may also or instead be employed without departing from the scope of this disclosure. Suitable devices are described, for example, in U.S. Pat. No. 9,596,997, issued on Mar. 21, 2017 and U.S. patent application Ser. No. 14/290,065 filed on May 29, 2014. The entire content of these applications is hereby incorporated by reference.

In general, Reflectance PhotoPlethysmoGraphy (RPPG) may be used for the detection of cardiac activity, which may provide for non-intrusive data collection, usability in wet, dusty and otherwise harsh environments, and low power requirements. In order to facilitate continuous use, the wearable system may include one, two or more sources of battery life, e.g., two or more batteries. In some embodiments, it may have a battery that can slip in and out of the head of the wearable system and can be recharged using an included accessory. Additionally, the wearable system may have a built-in battery so that, while the first battery is being charged, the wearable system and can still record data (during sleep, for example). In exemplary embodiments, the wearable system is enabled to automatically detect when the user is asleep, awake but at rest and exercising based on physiological data collected by the system.

Figure 2:
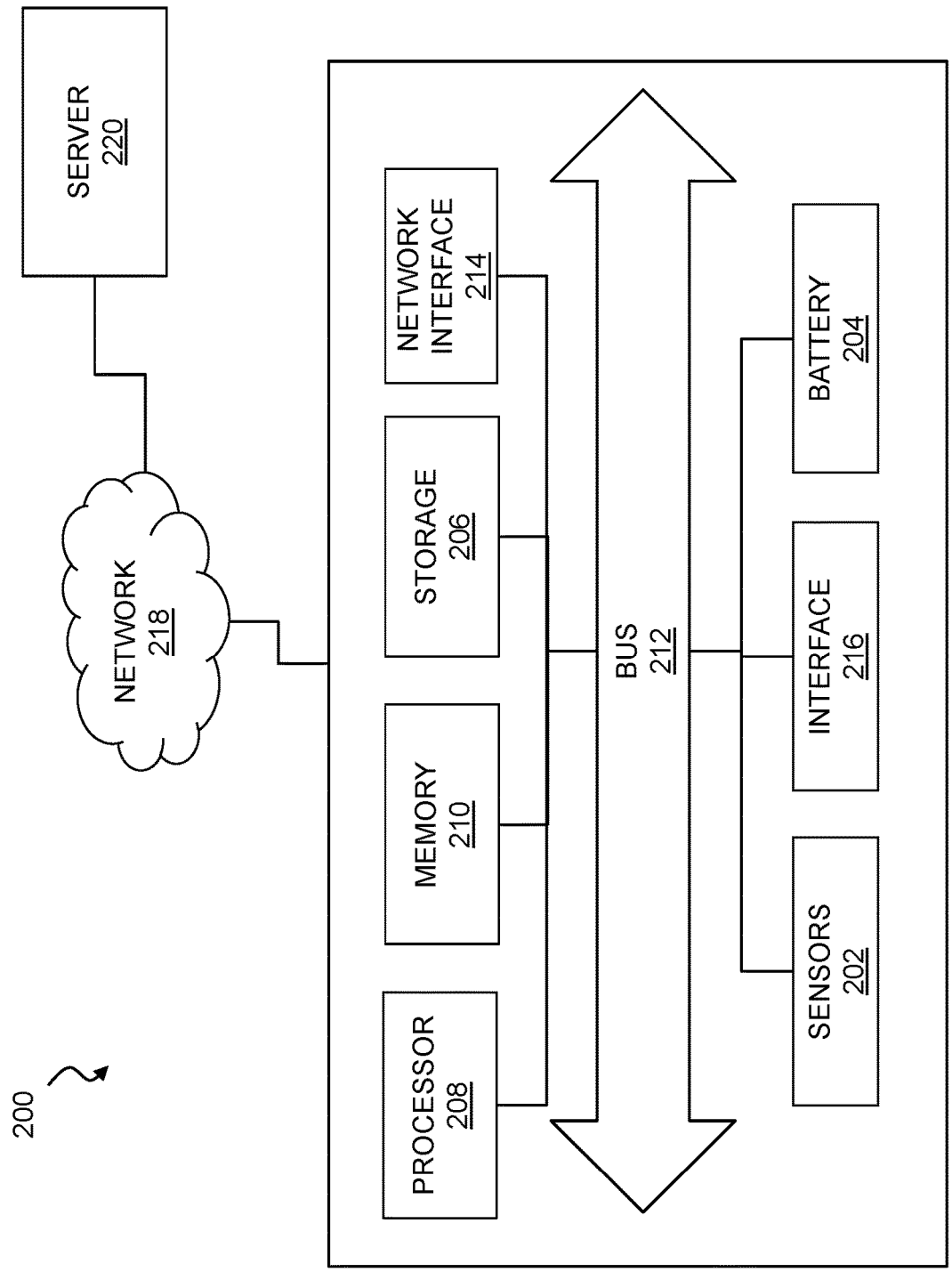
FIG. 2 shows a block diagram illustrating exemplary components of a device for continuous physiological monitoring.

FIG. 2 shows a block diagram illustrating exemplary components of a device for continuous physiological monitoring. The device 200, which may be a wearable device as generally described above, may generally include one or more sensors 202, a battery 204, storage 206, a processor 208, memory 210, a network interface 214, and a user interface 216.

The sensors 202 may include any sensor or combination of sensors suitable for heart rate monitoring as contemplated herein, as well as sensors 202 for detecting calorie burn, position (e.g., through a Global Positioning System or the like), motion, activity and so forth. The sensors 202 may include one or more sensors for activity measurement. In some embodiments, the system may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the wearable system may include a multi-axis accelerometer to measure motion and calculate distance. Motion sensors may be used, for example, to classify or categorize activity, such as walking, running, performing another sport, standing, sitting or lying down. The sensors 202 may, for example, include a thermometer for monitoring the user's body or skin temperature. In one embodiment, the sensors 202 may be used to recognize sleep based on a temperature drop, Galvanic Skin Response data, lack of movement or activity according to data collected by the accelerometer, reduced heart rate as measured by the heart rate monitor, and so forth. The body temperature, in conjunction with heart rate monitoring and motion, may be used to interpret whether a user is sleeping or just resting, as well as how well an individual is sleeping. The body temperature, motion, and other sensed data may also be used to determine whether the user is exercising, and to categorize and/or analyze activities as described in greater detail below. More generally, the sensors 202 may include any sensor or combination of sensors suitable for monitoring geographic location, physiological state, exertion, movement, and so forth in any manner useful for physiological monitoring as contemplated herein.

The battery 204 may include one or more batteries configured to allow continuous wear and usage of the wearable system. In one embodiment, the wearable system may include two or more batteries, such as a removable battery that may be removed and recharged using a charger, along with an integral battery that maintains operation of the device 200 while the main battery charges. In another aspect, the battery 204 may include a wireless rechargeable battery that can be recharged using a short range or long range wireless recharging system.

The storage 206 may include any computer-readable media for storing data collected by sensors 202 during operation of the device 200. This may include volatile or non-volatile memory, removable memory, and so forth.

The processor 208 may include any microprocessor, microcontroller, signal processor or other processor or combination of processors and other processing circuitry suitable for performing the processing steps described herein. In general, the processor 208 may be configured by computer executable code stored in the memory 210 to provide activity recognition and other physiological monitoring functions described herein.

The network interface 214 may be configured to wirelessly communicate data to a server 220, e.g., through an external network 218 such as any public or private network, or combination of the foregoing including, e.g., local area networks, the Internet, cellular data networks, and so forth. The network interface 214 may be used, e.g., to transmit raw or processed sensor data stored on the device 200 to the server 220, as well as to receive updates, receive configuration information, and otherwise communicate with remote resources and the user to support operation of the device.

The user interface 216 may include any components suitable for supporting interaction with a user. This may, for example include a keypad, display, buzzer, speaker, light emitting diodes, and any other components for receiving input from, or providing output to, a user. In one aspect, the device 200 may be configured to receive tactile input, such as by responding to sequences of taps on a surface of the device to change operating states, display information and so forth.

Figure 3:
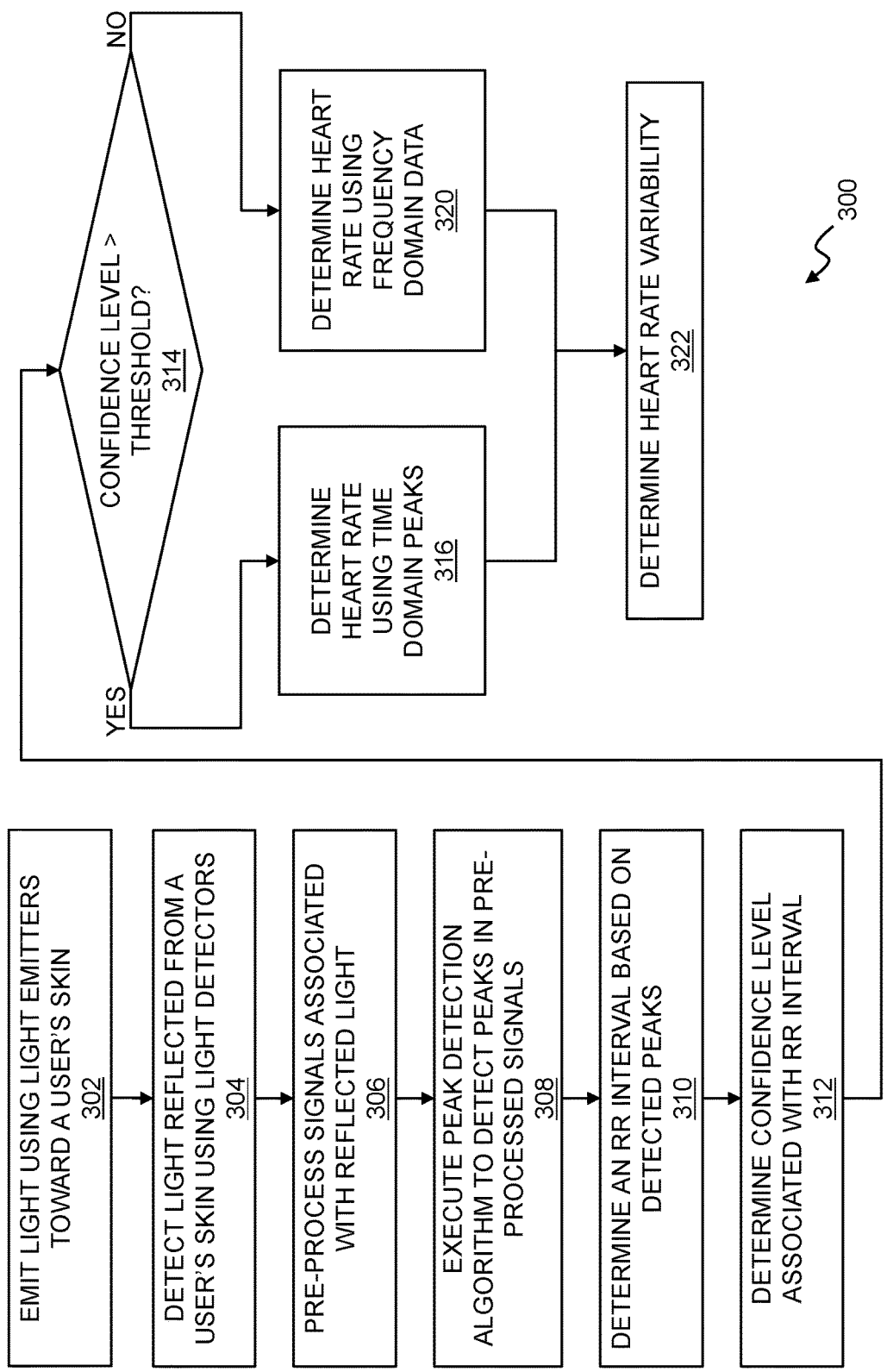
FIG. 3 is a flow chart illustrating a method for acquiring heart rate data.

FIG. 3 is a flow chart illustrating a method for acquiring heart rate data.

As shown in step 302, the method 300 may include emitting light toward a user's skin, e.g., from light emitters in a physiological monitoring device such as any of those described herein. As shown in step 304, light reflected from the user's skin may be detected at one or more light detectors positioned in the device, e.g., to detect light reflected from the light emitters. As shown in step 306, the method 300 may include pre-processing signals or data associated with the reflected light using any suitable technique to facilitate detection of heart beats. As shown in step 308, a processing module of the system may execute one or more computer-executable instructions associated with a peak detection algorithm to process data corresponding to the reflected light to detect a plurality of peaks associated with a plurality of beats of the user's heart. As shown in step 310, the processing module may determine an RR interval based on the plurality of peaks detected by the peak detection algorithm. As shown in step 312, the processing module may determines a confidence level associated with the RR interval.

Based on the confidence level associated with the RR interval estimate, the processing module may select either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, an implementation maintains the ability to obtain the RR intervals for as long as possible, even in the case of motion, thereby maximizing the information that can be extracted.

As shown in step 314, the method may include determining whether the confidence level associated with the RR interval is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, the method 300 may proceed to step 316, where the processing module uses a time domain technique such as detecting a plurality of peaks in time domain data to determine an instantaneous heart rate of the user. If the confidence level is not above the threshold, the method 300 may proceed to step 320, which may include determining a heart rate using frequency domain data such as a frequency transform of available time domain data. As shown in step 322, based on the instantaneous heart rate from step 316 or step 320, the method 300 may include determining a heart rate variability for the user based on a sequence of instantaneous heart rate measurements.

As described above, a system applying the method 300 described above may switch between different analytical techniques for determining a heart rate such as a statistical technique for detecting a heart rate and a frequency domain technique for detecting a heart rate. These two different modes have different advantages in terms of accuracy, processing efficiency, and information content, and as such may be useful at different times and under different conditions. Rather than selecting one such mode or technique as an attempted optimization, the system may usefully switch back and forth between these differing techniques, or other analytical techniques, using a predetermined criterion. The system may include a display device configured to render a user interface for displaying the sequence of the instantaneous heart rates of the user, the RR intervals and/or the heart rate variability determined by the processing module. The system may include a storage device configured to store the sequence of the instantaneous heart rates, the RR intervals and/or the heart rate variability determined by the processing module.

Figure 4:
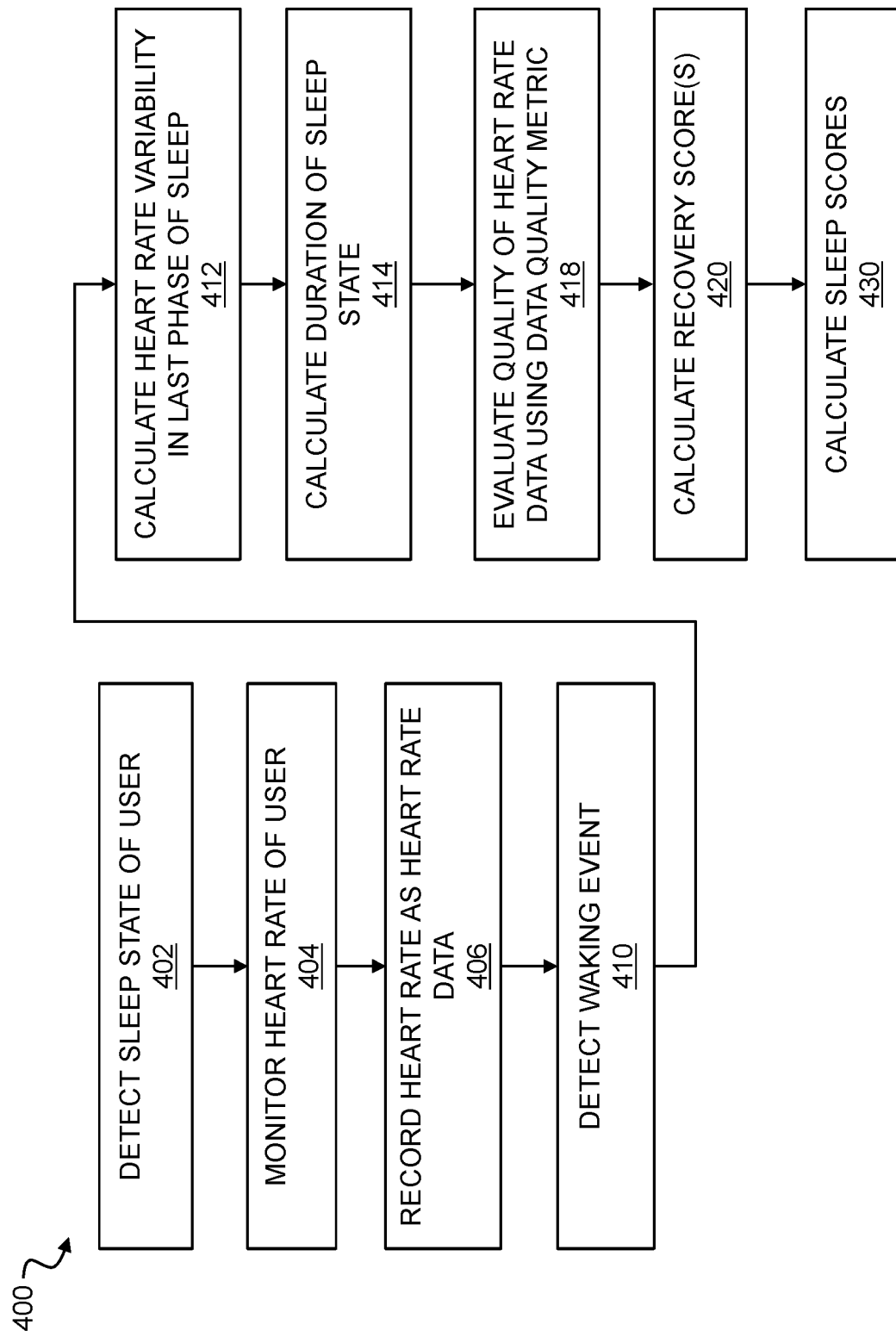
FIG. 4 is a flow chart illustrating a method for detecting heart rate variability in sleep states.

FIG. 4 is a flow chart illustrating a method for detecting heart rate variability in sleep states. The method 400 may be used in cooperation with any of the devices, systems, and methods described herein, such as by operating a wearable, continuous physiological monitoring device to perform the following steps. The wearable, continuous physiological monitoring system may for example include a processor, one or more light emitting diodes, one or more light detectors configured to obtain heart rate data from a user, and one or more other sensors to assist in detecting stages of sleep. In general, the method 400 aims to measure heart rate variability in the last phase of sleep before waking in order to provide a consistent and accurate basis for calculating a physical recovery score.

As shown in step 402, the method 400 may include detecting a sleep state of a user. This may, for example, include any form of continuous or periodic monitoring of sleep states using any of a variety of sensors or algorithms as generally described herein.

Sleep states (also be referred to as "sleep phases," "sleep cycles," "sleep stages," or the like) may include rapid eye movement (REM) sleep, non-REM sleep, or any states/stages included therein. The sleep states may include different phases of non-REM sleep, including Stages 1-3. Stage 1 of non-REM sleep generally includes a state where a person's eyes are closed, but the person can be easily awakened; Stage 2 of non-REM sleep generally includes a state where a person is in light sleep, i.e., where the person's heart rate slows and their body temperature drops in preparation for deeper sleep; and Stage 3 of non-REM sleep generally includes a state of deep sleep, where a person is not easily awakened. Stage 3 is often referred to as delta sleep, deep sleep, or slow wave sleep (i.e., from the high amplitude but small frequency brain waves typically found in this stage). Slow wave sleep is thought to be the most restful form of sleep, which relieves subjective feelings of sleepiness and restores the body.

REM sleep on the other hand typically occurs 1-2 hours after falling asleep. REM sleep may include different periods, stages, or phases, all of which may be included within the sleep states that are detected as described herein. During REM sleep, breathing may become more rapid, irregular and shallow, eyes may jerk rapidly (thus the term "Rapid Eye Movement" or "REM"), and limb muscles may be temporarily paralyzed. Brain waves during this stage typically increase to levels experienced when a person is awake. Also, heart rate, cardiac pressure, cardiac output, and arterial pressure may become irregular when the body moves into REM sleep. This is the sleep state in which most dreams occur, and, if awoken during REM sleep, a person can typically remember the dreams. Most people experience three to five intervals of REM sleep each night.

Homeostasis is the balance between sleeping and waking, and having proper homeostasis may be beneficial to a person's health. Lack of sleep is commonly referred to as sleep deprivation, which tends to cause slower brain waves, a shorter attention span, heightened anxiety, impaired memory, mood disorders, and general mental, emotional, and physical fatigue. Sleep debt (the effect of not getting enough sleep) may result in the diminished abilities to perform high-level cognitive functions. A person's circadian rhythms (i.e., biological processes that display an endogenous, entrainable oscillation of about 24 hours) may be a factor in a person's optimal amount of sleep. Thus, sleep may in general be usefully monitored as a proxy for physical recovery. However, a person's heart rate variability at a particular moment during sleep—during the last phase of sleep preceding a waking event—can further provide an accurate and consistent basis for objectively calculating a recovery score following a period of sleep.

According to the foregoing, sleep of a user may be monitored to detect various sleep states, transitions, and other sleep-related information. For example, the device may monitor/detect the duration of sleep states, the transitions between sleep states, the number of sleep cycles or particular states, the number of transitions, the number of waking events, the transitions to an awake state, and so forth. Sleep states may be monitored and detected using a variety of strategies and sensor configurations according to the underlying physiological phenomena. For example, body temperature may be usefully correlated to various sleep states and transitions. Similarly, galvanic skin response may be correlated to sweating activity and various sleep states, any of which may also be monitored, e.g., with a galvanic skin response sensor, to determine sleep states. Physical motion can also be easily monitored using accelerometers or the like, which can be used to detect waking or other activity involving physical motion. In another aspect, heart rate activity itself may be used to infer various sleep states and transitions, either alone or in combination with other sensor data. Other sensors may also or instead be used to monitor sleep activity, such as brain wave monitors, pupil monitors, and so forth, although the ability to incorporate these types of detection into a continuously wearable physiological monitoring device may be somewhat limited depending on the contemplated configuration.

As shown in step 404, the method 400 may include monitoring a heart rate of the user substantially continuously with the continuous physiological monitoring system. Continuous heart rate monitoring is described above in significant detail, and the description is not repeated here except to note generally that this may include raw sensor data, heart rate data or peak data, and heart rate variability data over some historical period that can be subsequently correlated to various sleep states and activities.

As shown in step 406, the method 400 may include recording the heart rate as heart rate data. This may include storing the heart rate data in any raw or processed form on the device, or transmitting the data to a local or remote location for storage. In one aspect, the data may be stored as peak-to-peak data or in some other semi-processed form without calculating heart rate variability. This may be useful as a technique for conserving processing resources in a variety of contexts, for example where only the heart rate variability at a particular time is of interest. Data may be logged in some unprocessed or semi-processed form, and then the heart rate variability at a particular point in time can be calculated once the relevant point in time has been identified.

As shown in step 410, the method 400 may include detecting a waking event at a transition from the sleep state of the user to an awake state. It should be appreciated that the waking event may be a result of a natural termination of sleep, e.g., after a full night's rest, or in response to an external stimulus that causes awakening prior to completion of a natural sleep cycle. Regardless of the precipitating event(s), the waking event may be detected via the various physiological changes described above, or using any other suitable techniques. While the emphasis herein is on a wearable, continuous monitoring device, it will be understood that the device may also receive inputs from an external device such as a camera (for motion detection) or an infrared camera (for body temperature detection) that can be used to aid in accurately assessing various sleep states and transitions.

Thus, the wearable, continuous physiological monitoring system may generally detect a waking event using one or more sensors including, for example, one or more of an accelerometer, a galvanic skin response sensor, a light sensor, and so forth. For example, in one aspect, the waking event may be detected using a combination of motion data and heart rate data.

As shown in step 412, the method 400 may include calculating a heart rate variability of the user at a moment in a last phase of sleep preceding the waking event based upon the heart rate data. While a waking event and a history of sleep states are helpful information for assessing recovery, the method 400 described herein specifically contemplates use of the heart rate variability in a particular last phase of sleep as a consistent foundation for calculating recovery scores for a device user. Thus, step 412 may also include detecting a most recent slow wave sleep period immediately prior to the waking event, or otherwise determining the end of a slow wave or deep sleep episode immediately preceding the waking event.

It will be appreciated that the last phase of sleep preceding a natural waking event may be slow wave sleep. However, where a sleeper is awakened prematurely, this may instead include a last recorded episode of REM sleep or some other phase of sleep immediately preceding the waking event. In one aspect, this heart rate variability may be used. However, the end of a particular phase of sleep may provide a more consistent benchmark for assessing recovery. Thus, in such premature waking instances, a prior history may be reviewed to locate a point in time at or near the end of a particular phase of sleep, such as slow wave sleep or any other useful benchmark. This moment—the end of the last phase of slow wave sleep (or any other suitable phase) before waking—is the point at which heart rate variability data provides the most accurate and consistent indicator of physical recovery. Thus, with the appropriate point of time identified, the historical heart rate data (in whatever form) may be used with the techniques described above to calculate the corresponding heart rate variability.

It will be further noted that the time period for this calculation may be selected with varying degrees of granularity depending on the ability to accurate detect the last phase of sleep and an end of the last phase of sleep. Thus, for example, the time may be a predetermined amount of time before waking, or at the end of slow wave sleep, or some predetermined amount of time before the end of slow wave sleep is either detected or inferred. In another aspect, an average heart rate variability or similar metric may be determined for any number of discrete measurements within a window around the time of interest. Thus, for example, heart rate variability may be measured over one minute, or some other interval, preceding the end of the relevant phase (e.g., slow wave sleep), and this may be used to provide a consistent benchmark from sleep event to sleep event, and among different users.

As shown in step 414, the method 400 may include calculating a duration of the sleep state. The quantity and quality of sleep may be highly relevant to physical recovery, and as such the duration of the sleep state may be used to calculate a recovery score.

As shown in step 418, the method 400 may include evaluating a quality of heart rate data using a data quality metric for a slow wave sleep period, e.g., the slow wave sleep period occurring most recently before the waking event. As noted above, the quality of heart rate measurements may vary over time for a variety of reasons. Thus, the quality of heart rate data may be evaluated prior to selecting a particular moment or window of heart rate data for calculating heart rate variability, and the method 400 may include using this quality data to select suitable values for calculating a recovery score. For example, the method 400 may include calculating the heart rate variability for a window of predetermined duration within the slow wave sleep period having the highest quality of heart rate data according to the data quality metric.

As shown in step 420, the method 400 may include calculating a recovery score for the user based upon the heart rate variability from the last phase of sleep. The calculation may be based on other sources of data. For example, the calculation of recovery score may be based on the duration of sleep, the stages of sleep detected or information concerning the stages (e.g., amount of time in certain stages), information regarding the most recent slow wave sleep period or another sleep period/state, information from the GSR sensor or other sensor(s), and so on. The method 400 may further include calculating additional recovery scores after one or more other waking events of the user for comparison to the previously calculated recovery score. The actual calculation of a discovery score is described in substantial detail above, and this description is not repeated here except to note that the use of a heart rate variability measurement from the last phase of sleep provides an accurate and consistent basis for evaluating the physical recovery state of a user following a period of sleep.

As shown in step 430, the method 400 may include calculating a sleep score and communicating this score to a user.

In one aspect, the sleep score may be a measure of prior sleep performance. For example, a sleep performance score may quantify, on a scale of 0-100, the ratio of the hours of sleep during a particular resting period compared to the sleep needed. On this scale, if a user sleeps six hours and needed eight hours of sleep, then the sleep performance may be calculated as 75%. The sleep performance score may begin with one or more assumptions about needed sleep, based on, e.g., age, gender, health, fitness level, habits, genetics, and so forth and may be adapted to actual sleep patterns measured for an individual over time.

The sleep score may also or instead include a sleep need score or other objective metric that estimates an amount of sleep needed by the user of the device in a next sleep period. In general, the score may be any suitable quantitative representation including, e.g., a numerical value over some predetermined scale (e.g., 0-10, 1-100, or any other suitable scale) or a representation of a number of hours of sleep that should be targeted by the user. In another aspect, the sleep score may be calculated as the number of additional hours of sleep needed beyond a normal amount of sleep for the user.

The score may be calculated using any suitable inputs that capture, e.g., a current sleep deficit, a measure of strain or exercise intensity over some predetermined prior interval, an accounting for any naps or other resting, and so forth. A variety of factors may affect the actual sleep need, including physiological attributes such as age, gender, health, genetics and so forth, as well as daytime activities, stress, napping, sleep deficit or deprivation, and so forth. The sleep deficit may itself be based on prior sleep need and actual sleep performance (quality, duration, waking intervals, etc.) over some historical window. In one aspect, an objective scoring function for sleep need may have a model of the form:

$$\text{SleepNeed} = \text{Baseline} + f_1(\text{strain}) + f_2(\text{debt}) - \text{Naps}$$

In general, this calculation aims to estimate the ideal amount of sleep for best rest and recovery during a next sleep period. When accounting for time falling asleep, periods of brief wakefulness, and so forth, the actual time that should be dedicated to sleep may be somewhat higher, and this may be explicitly incorporated into the sleep need calculation, or left for a user to appropriately manage sleep habits.

In general, the baseline sleep may represent a standard amount of sleep needed by the user on a typical rest day (e.g., with no strenuous exercise or workout). As noted above, this may depend on a variety of factors, and may be estimated or measured for a particular individual in any suitable manner. The strain component, $f_1(\text{strain})$, may be assessed based on a previous day's physical intensity, and will typically increase the sleep need. Where intensity or strain is measured on an objective scale from 0 to 21, the strain calculation may take the following form, which yields an additional sleep time needed in minutes for a strain, i:

$$f(i) = \frac{1.7}{1 + e^{\frac{17-i}{3.5}}}$$

The sleep debt, $f_2(\text{debt})$, may generally measure a carry-over of needed sleep that was not attained in a previous day.

This may be scaled, and may be capped at a maximum, according to individual sleep characteristics or general information about long term sleep deficit and recovery. Naps may also be accounted for directly by correcting the sleep need for any naps that have been taken, or by calculating a nap factor that is scaled or otherwise manipulated or calculated to more accurately track the actual effect of naps on prospective sleep need.

However calculated, the sleep need may be communicated to a user, such as by displaying a sleep need on a wrist-worn physiological monitoring device, or by sending an e-mail, text message or other alert to the user for display on any suitable device.

In addition to sleep detection, a device such as any of the wearable physiological monitoring devices described herein may also or instead automatically detect activities such as workouts and the like. A technique suitable for deployment on a wearable physiological monitoring device is described in greater detail below.

Figure 5:
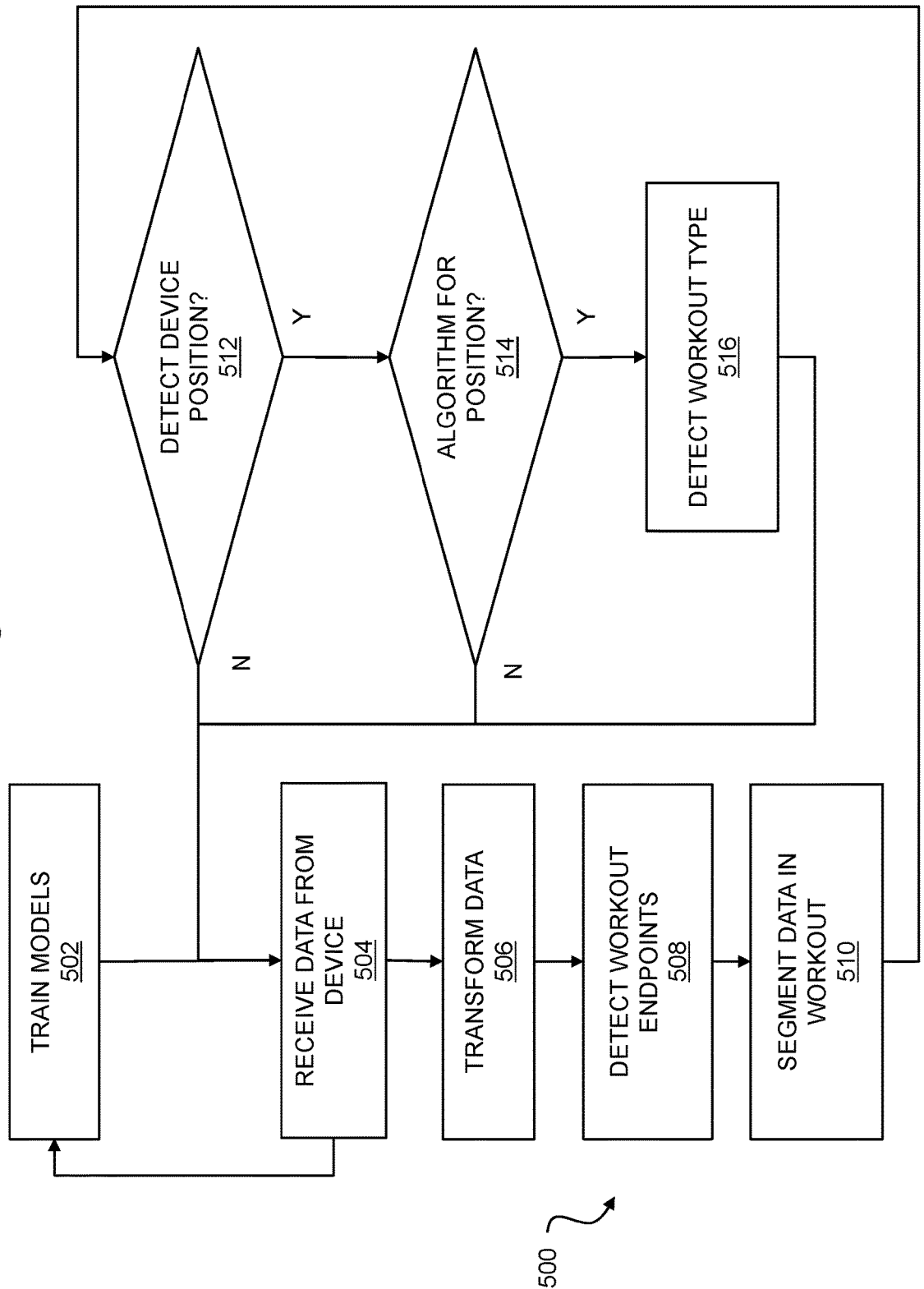
FIG. 5 is a flow chart illustrating a method for automated activity detection.

FIG. 5 is a flow chart illustrating a method for automated activity detection, e.g., a method of determining the timing and classification of a workout. In general, the technique described below determines starting and ending points for a workout, e.g., using a workout detection algorithm. Provided that the workout meets predetermined criteria for heart rate and motion, and further provided that a location of the monitor on a user's body can be determined, a workout classification algorithm may be used to automatically determine a user's activity. Thus, the workout classification process may be sequenced to facilitate use of a deep convolutional neural network (or similar artificial intelligence tool) only when data suitable for the neural network is available. This filtering and identification strategy permits the creation of a compact, dedicated neural network that can be selectively employed only when it is likely to produce meaningful results. As a significant advantage, this phased approach yields a more compact, computationally efficient model that facilitates real time workout recognition and permits deployment of the entire workout recognition algorithm on a wearable device even when the device has limited computational resources selected to reduce size and preserve battery life.

As shown in step 502, the method 500 may include training models such as machine learning models to assist in the activity recognition process. In general, this may begin by acquiring data from a number of users of a wearable physiological monitor over time, which may include labeled data, e.g., where a user self-identifies activities, unlabeled data, or some combination of these.

In one aspect, this includes training models for position detection and workout recognition using data from wearers of physiological monitoring devices. Using accumulated data from such systems, which may include heart rate and accelerometer data with user-reported and self-labeled activities for e.g., thousands of users, a process can be developed to pick out a workout from a stream of gathered biometric data. Then, artificial intelligence techniques such as a deep convolutional neural network may be used to classify a sport or other activity being performed during such a workout.

This process may use a variety of different machine learning tools or the like. In one aspect, training the models may include training a machine learning algorithm or other artificial intelligence tool to estimate a probability of a location of a wearable physiological monitor on a body of the user using data from an accelerometer in the wearable physiological monitor, which may be used as described below to derive a probability-based estimate of the location. This may also or instead include training a machine learning algorithm or other artificial intelligence tool or the like to estimate a probability of a location based on heart rate data from the monitor instead of, or in addition to, the accelerometer data. In another aspect, training the models may include training a model for auto-classification of a workout, such as by training a deep convolutional neural network to calculate a probability that a chunk of data including at least one of accelerometer data and heart rate data from the wearable physiological monitor during the workout is each of a number of candidate types for the workout.

It will be understood that models such as an automatic workout classification algorithm may be continuously updated over time as new user data becomes available. Thus, in one aspect, the method 500 may include receiving data from a group of users and updating the automatic workout classification algorithm and/or other models such as the position detection model based on a continuous stream of new user data. This data may be updated on a central server or other suitable facility based on new data from a plurality of existing users, from new users, or some combination of these, and models may be updated on any suitable schedule. Determining the position of the wearable physiological monitor on a body of a user may similarly include training a machine learning algorithm to identify the position and then updating the machine learning algorithm on a central server based on new data from a plurality of users.

In another aspect, the method 500 may include customizing the automatic workout classification algorithm for a particular user over time or otherwise adapting the automatic classification algorithm to a specific user based on prior workout data for the specific user. As a user creates and labels workout data, the models may learn temporal patterns such as when workouts typically begin and end, as well as the types of workouts typical for a user. Thus, for example, if a user consistently jogs several miles each morning, and plays tennis on Tuesday and Friday evenings, this user history may be incorporated into a user-specific model and applied prospectively for more accurate workout type classification. This may be particularly useful, for example, in discriminating among activities where a number of different types of sports, e.g., racquetball, tennis, and squash, have similar motion patterns. According to the foregoing, in one aspect, the automatic workout classification algorithm may detect the type of the workout based on a history of exercise for the user. This may include training the classification algorithm with user-specific data, or more heavily weighting user-specific data during training. This may also or instead include using independent discriminators, filters, rules, or the like based on observed user-specific data.

As shown in step 504, the method 500 may include receiving data from a device such as a wearable physiological monitor, such as accelerometer data and heart rate data acquired by the wearable physiological monitor while being worn by a user. In general, receiving data in this context may include receiving data into a memory on the device, e.g., for local analysis, or receiving data at a remote server, or some combination of these. The remote server may be used, e.g., to process the data and report results to a user concerning workout classifications, or to aggregate the data with other data for updating or refining a machine learning algorithm or the like.

As shown in step 506, the method may include transforming data into a form suitable for detection of activity such as a workout. In general, both heart rate data and accelerometer data may be useful in discriminating between workouts and non-workout activities. However, these data types can have different magnitudes, frequencies, and distributions that render it difficult to form useful conclusions based on a concurrent use of both data types. To address this variability, the heart rate data and/or accelerometer data may be transformed, e.g., into the log domain, where acceleration data appears to generally follow a lognormal distribution (logarithm of continuous probability of a random variable is normally distributed) while heart rate data appears to generally follow a normal distribution. The data can be added and further logarithmically transformed to provide a single, normally distributed variable that is separable beyond a standard deviation for workout versus non-workout activity. The probability of a workout can then be estimated using probability distributions for workout and non-workout activities based on the transformed and combined data. Further, when a workout is detected, a true/false discriminator may be applied to confirm or reject the identification based on, e.g., a model trained using a sample of known workout and non-workout activity using any suitable parameters, preferably uncorrelated parameters, derived from the heart rate and/or accelerometer data in a linear discriminant analysis or the like.

As shown in step 508, the method 500 may include identifying a workout by a user of the wearable physiological monitor based on the heart rate data and the accelerometer data. For example, this may include detecting workout endpoints that mark a timewise beginning and end of a workout, such as by applying a threshold based on the accelerometer data and the heart rate data to identify two endpoints of an interval of increased physical activity indicative of a workout by a user of the wearable physiological monitor. This may more generally include any suitable technique for automatically identifying or selecting two endpoints of a workout.

As shown in step 510, the method 500 may include segmenting the data in a workout, such as by dividing the data including the accelerometer data and the heart rate data into a number of sequential segments. This segmenting approach advantageously facilitates segment-by-segment processing of the transformed data in order to locally apply a probabilistic technique to individual segments in order to determine a position of the device on a user's body.

As shown in step 512, the method 500 may include detecting a position of the wearable physiological monitor on a body of the user during the workout. This may begin, for example, by applying a machine learning algorithm or any other suitable algorithm to each of the number of sequential segments of the accelerometer data (and optionally heart rate data where this provides additional information useful for discriminating among device positions) to determine a probability that each one of the number of sequential segments includes data from one or more locations on a body of the user. This may further include selecting one of the one or more locations having a highest overall probability of being a current position from all of the number of sequential segments, and using this selected position as a position of the wearable physiological monitor on the body of the user. Or stated otherwise, determining the position may include determining the position based on one of a number of candidate positions from among the candidates created by the machine learning algorithm for any of the number of sequential segments that has the highest overall probability, aggregated across all of the segments, of being an actual position of the wearable physiological monitor.

This step may also or instead be implemented to specifically detect predetermined positions that have corresponding auto-classification models. Thus, determining the position may include identifying the position from a plurality of predetermined positions including the number of predetermined positions on the body for which the automatic workout classification algorithm is configured to detect a type of workout. The number of predetermined positions may include one or more of a wrist and an ankle. Other positions, such as the forearm and the bicep may also be used for positioning a wearable device, and may be one of the predetermined positions as contemplated herein. In one aspect, any other position, whether identified or not, may result in a nominal failure to detect a position if there is no corresponding workout auto-classification model available.

The position of a wearable physiological monitoring device may also or instead inform different modes of an existing algorithm, or be used to choose/select different algorithms for running on a system. For example, knowing the position of the device may improve the accuracy of workout auto-detection and classification (e.g., classifying cycling from the wrist may not be preferred, but classifying from the leg/ankle would be preferred).

If a position cannot be detected, the method 500 may return to step 504 and further data may be received from sensors of the device for analysis. In this case, the method 500 may generally include additional steps of receiving additional data from the wearable physiological monitor and identifying a second workout as previously described. If a position is detected, the method 500 may proceed to step 514 for position-based processing.

It should also be appreciated that the order of steps preceding the workout classification may be altered. For example, while the figure illustrates workout detection preceding position detection, a position of the device may instead be continuously monitored, and a threshold workout detection may only be performed when the device is in one or more predetermined locations on a body of the user/wearer.

As shown in step 514, the method 500 may include conditionally employing an automatic workout classification algorithm to detect a type of the workout when the position is one of a number of predetermined positions on the body for which the automatic workout classification algorithm is configured to detect the type. For example, if a classification algorithm is only available for a wrist-worn device, step 514 may include conditionally employing an automatic workout classification algorithm to detect a type of the workout only when the position is a wrist of the user. If the position detected in step 512 is a position for which there is an automatic workout classification, then the method 500 may proceed to step 516 where a workout can be automatically classified. If the position detected in step 512 is a position for which there is not an automatic workout classification, then the method 500 may return to step 504 where additional data can be received from sensors of the device.

Additional processing steps may be performed. For example, selecting an algorithm as shown in step 514 may also or instead include determining whether a different position for the wearable physiological monitor can provide more accurate data for the type of the workout. When the position is identified and a different position can provide more accurate data (particularly when the different position can provide substantially more accurate data), the method 500 may include providing a notification to the user suggesting a movement of the wearable physiological monitor to the different position.

As shown in step 516, the method 500 may include detecting a workout type. As described above, by constraining this inquiry to a known workout interval and data from a particular device location, the automated type determination becomes a tractable computing problem amenable to the use of artificial intelligence techniques such as a deep convolutional neural network.

Thus in one aspect, detecting the workout type may include conditionally detecting the workout type with an automatic workout classification algorithm including a deep convolutional neural network trained to calculate a probability that a chunk of data including at least one of accelerometer data and heart rate data from the wearable physiological monitor during the workout is each of a number of candidate types for the workout. More specifically, this may include applying the deep convolutional neural network to a number of chunks of data from the wearable physiological monitor to obtain a posterior distribution of the number of candidate types for the workout. The workout type may then be determined by selecting one of the number of candidate types in the posterior distribution having a highest probability of characterizing a workout type for the workout. An example of a type detection algorithm using a deep convolutional neural network as contemplated in step 516 is now described in greater detail.

The data for a workout interval may be divided into chunks or segments. For example, the workout may be split into smaller chunks that have some minimum total acceleration. This may include dividing the data into tensors, where the tensors contain accelerometer magnitude, as well as x, y, and z dimensional data. For each chunk received, a splitting procedure may be applied based on the amount of total accelerometer magnitude within some n-minute chunk. An example splitting procedure would be a 20-minute running activity that is split into four total 5-minute chunks, where each chunk has some minimum amount of total acceleration above a threshold.

Each chunk may be scored using a deep convolutional neural network for activities. The objective of the deep convolutional neural network in this context is to compute the probability that a chunk belongs to a pre-defined workout category. In certain implementations, examples of these categories may include "running," "weightlifting," and "cycling," for which there may be a labeled dataset in the training sets for the neural network. Each input to the network is a collection of mini-batched n-minute chunks, represented by a tensor of three-dimensional accelerometer data. Each chunk may pass through four instances of a convolutional block including a convolutional operator that computes abstractions of the incoming data, and then passes that output through a non-linear activation function. The data may then be post-processed via a normalization operator. The last step may include block-pooling of adjacent elements in the tensor with an averaging function. Once the convolutional blocks have completed their computations, the model may use a combination of tensor-tensor dot products, non-linear activations, dropout algorithms, and normalization operators to compute the probability of a given chunk being a specific workout. As noted above, this neural network may be trained using training sets including labeled data from a group of users. While clustering or unsupervised learning is also suitable, the initial use of labeled data sets can provide more efficient training for discriminating among human-recognizable categories of activities such as specific sports or exercise types.

Standard convolutional neural networks may have strict API rules, particularly with the shape of the input data. Because workouts are generally variable in length, it may be advantageous to split the workout into K-minute chunks and classify based on that information. Thus, each input to the convolutional neural network may be shaped with three channels, with each channel corresponding to a K-minute one-dimensional array. Each chunk may then be mapped to the sport or activity to which the workout belonged. Pre-processing may be minimal, where the enforcement of orientation, continuity, and magnitude are the only hurdles. For orientation, while the user is provided information on a correct manner to orient the wearable physiological device, there may be no reliable way to enforce this orientation. Additionally, the handedness of a user can affect the read out of the accelerometer data. Transforming and scaling input data by user characteristics may enforce this notion. For continuity, the user removing their wearable physiological device during an activity, or in some way losing data, could negatively affect results. Thus, simple logic may be included to verify that there are no relatively large gaps in data. For magnitude, in order to verify the model is training on movement, a minimum magnitude of motion may be enforced for each potential sample.

In one aspect, each timewise chunk of data may have one or more activities and corresponding probabilities based on the output of the neural network. The chunks may be aggregated on their mean scores for each activity. In order to select a particular type of workout activity, the probabilities for these chunks are combined into an aggregated score in order to determine the probability that one activity is significantly more likely than the rest. If the probability is sufficiently high, the activity is classified, e.g., as one of the example categories or else it is marked as an unknown activity category. The output matrix from the network may include probabilities of each class on a per chunk basis. In one aspect, each model may output probabilities based exclusively on K-minute chunks. Because each activity often includes many chunks, the opportunity arises to intelligently determine an aggregate result. If it is assumed that each column forms a probability distribution for a particular sport or activity, a group of parametrized distributions can be compared from all rows and columns, such as:

$$\begin{bmatrix} .15 & .1 & .1 & .65 \\ .10 & .05 & .05 & .80 \\ .25 & .025 & .025 & .70 \\ .60 & .05 & .05 & .30 \end{bmatrix} \rightarrow \mu = \begin{bmatrix} .275 \\ .056 \\ .056 \\ .613 \end{bmatrix}, \sigma = \begin{bmatrix} .195 \\ .027 \\ .027 \\ .188 \end{bmatrix}$$

If it is assumed that the model outputs roughly normally distributed values, and some reasonable prior values for the parameters are established, a posterior distribution can be created, and each workout can be expressed as a posterior distribution. Once a posterior for each sport or activity column is acquired, a probability can be computed that one of the probability distributions is larger than all the others. If that probability for one of the types of workouts is sufficiently high (P(B>A)>T), the workout can be classified to the corresponding type.

The method 500 may then return to step 504 where further data may be received and the process may continue.

Several advantages accrue to processing data in this manner. By initially restricting workout detection to intervals where a workout is detected, the overall detection scheme can be run continuously on a wearable device, with a simple initial filter (workout detection) for further processing. Further, by limiting use of a workout type detection algorithm such as a deep convolutional neural network to those situations in which the algorithm can produce meaningful results—when a workout is occurring and a position on the body has a corresponding detection model—the device can reduce or avoid the use of battery power and processing resources under conditions that are poor candidates for workout type detection. Additionally, by training the model for a more limited number of detection conditions, the size and complexity of the neural network can also be significantly reduced, thus permitting deployment, e.g., on a wearable device or other capacity constrained platform where memory or processing resources are limited.

According to the foregoing, there is also disclosed herein a wearable physiological monitoring device incorporating the features discussed above. Thus in one aspect, there is disclosed herein a system including a wearable housing, one or more sensors in the wearable housing configured to provide heart rate data and accelerometer data for a user of the wearable housing, a memory, and a processor. The processor may be configured by computer executable code stored in the memory to identify a workout by the user based on the heart rate data and the accelerometer data, determine a position of the wearable housing on a body of the user during the workout, and conditionally employ an automatic workout classification algorithm to detect a type of the workout when the position is one of a number of predetermined positions on the body for which the automatic workout classification algorithm is configured to detect the type. The processor may also be configured to conditionally employ the automatic workout classification algorithm to detect the type of the workout only when the position is a wrist of the user. The processor may further be configured to create a notification to the user to move the wearable housing to a different position when the position is not one of the number of predetermined positions on the body for which the automatic workout classification algorithm is configured to detect the type. As discussed above, the automatic workout classification algorithm may include a deep convolutional neural network trained to calculate a probability that a chunk of data including at least one of accelerometer data and heart rate data from the one or more sensors during the workout is each of a number of candidate types for the workout.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A computer program product comprising computer executable code embodied in a non-transitory computer-readable medium that, when executing on a wearable physiological monitor, performs the steps of:
    receiving data from a number of sensors on the wearable physiological monitor, the data including accelerometer data and heart rate data acquired by the wearable physiological monitor;
    applying a threshold based on the accelerometer data and the heart rate data to identify two endpoints of an interval of increased physical activity indicative of a workout by a user of the wearable physiological monitor;
    dividing the data including the accelerometer data and the heart rate data into a number of sequential segments;
    determining a probability that each one of a number of sequential segments of accelerometer data includes data from one or more locations on a body of the user by applying a machine learning algorithm to each one of the number of sequential segments;
    selecting one of the one or more locations having a highest overall probability of being a current position from all of the number of sequential segments as a position of the wearable physiological monitor on the body of the user; and
    conditionally employing an automatic workout classification algorithm to detect a type of the workout only when the position is a wrist of the user, wherein the automatic workout classification algorithm includes a deep convolutional neural network trained to calculate a probability that a chunk of data including at least one of accelerometer data and heart rate data from the wearable physiological monitor during the workout is each of a number of candidate types for the workout.

2. The computer program product of claim 1 wherein the automatic workout classification algorithm detects the type of the workout based on a history of exercise for the user.

3. A method for exercise monitoring comprising:
    receiving data from a wearable physiological monitor, the data including accelerometer data and heart rate data acquired by the wearable physiological monitor;
    identifying a workout by a user of the wearable physiological monitor based on the heart rate data and the accelerometer data;
    training a machine learning algorithm to estimate a probability of a location of the wearable physiological monitor on a body of the user using data from an accelerometer;
    determining a probability of the location for each of a number of sequential segments of the accelerometer data from the workout by applying the machine learning algorithm to each one of the number of sequential segments of the accelerometer data;
    determining a position on the body of the user based on one of a number of candidate positions having a highest overall probability of being an actual position of the wearable physiological monitor for the number of sequential segments based on an aggregated probability of each candidate position across all of the sequential segments; and
    conditionally employing an automatic workout classification algorithm to detect a type of the workout when the position is one of a number of predetermined positions on the body for which the automatic workout classification algorithm is configured to detect the type, wherein the automatic workout classification algorithm includes a deep convolutional neural network trained to calculate a probability that a chunk of data including at least one of accelerometer data and heart rate data from the wearable physiological monitor during the workout is each of a number of candidate types for the workout.

4. The method of claim 3 wherein identifying the workout includes applying a threshold based on at least one of the accelerometer data and the heart rate data to select two endpoints of the workout.

5. The method of claim 3 wherein conditionally employing the automatic workout classification algorithm includes applying the automatic workout classification algorithm only when the position is a wrist of the user.

6. The method of claim 3 further comprising applying the deep convolutional neural network to a number of chunks of data from the wearable physiological monitor to obtain a posterior distribution of the number of candidate types for the workout.

7. The method of claim 6 further comprising determining the type of the workout by selecting one of the number of candidate types in the posterior distribution having a highest probability of characterizing a workout type for the workout.

8. The method of claim 3 further comprising updating the automatic workout classification algorithm on a central server based on new data from a plurality of users.

9. The method of claim 3 wherein training the machine learning algorithm includes updating the machine learning algorithm on a central server based on new data from a plurality of users.

10. The method of claim 3 further comprising adapting the automatic workout classification algorithm to a specific user based on prior workout data for the specific user.

11. The method of claim 3 further comprising, when the position cannot be determined during the workout, receiving additional data from the wearable physiological monitor and identifying a second workout.

12. The method of claim 3 further comprising determining whether a different position for the wearable physiological monitor can provide more accurate data for the type of the workout and, when the different position can provide more accurate data, providing a notification to the user suggesting a movement of the wearable physiological monitor to the different position.

13. A system comprising:
a wearable housing;
one or more sensors in the wearable housing configured to provide heart rate data and accelerometer data for a user of the wearable housing;
a memory storing a machine learning algorithm that estimates a probability of a location of the wearable housing on a body of the user using data from an accelerometer; and
a processor configured by computer executable code stored in the memory to identify a workout by the user based on the heart rate data and the accelerometer data, determining a probability of a position on the body of the user for each of a number of sequential segments of the accelerometer data by applying the machine learning algorithm to each of the number of sequential segments of the accelerometer data from the workout and selecting the position on the body of the user based on one of a number of candidate positions having a highest overall probability of being an actual position of the wearable housing for the number of sequential segments, and conditionally employ an automatic workout classification algorithm to detect a type of the workout when the position is one of a number of predetermined positions on the body for which the automatic workout classification algorithm is configured to detect the type, wherein the automatic workout classification algorithm includes a deep convolutional neural network trained to calculate a probability that a chunk of data including at least one of accelerometer data and heart rate data from the wearable physiological monitor during the workout is each of a number of candidate types for the workout.

14. The system of claim 13 wherein the processor is configured to conditionally employ the automatic workout classification algorithm to detect the type of the workout only when the position is a wrist of the user.

15. The system of claim 13 wherein the processor is configured to create a notification to the user to move the wearable housing to a different position when the position is not one of the number of predetermined positions on the body for which the automatic workout classification algorithm is configured to detect the type.

* * * * *